United States Patent
Mountney et al.

(10) Patent No.: US 9,681,856 B2
(45) Date of Patent: Jun. 20, 2017

(54) IMAGE FUSION FOR INTERVENTIONAL GUIDANCE

(71) Applicants: Peter Mountney, London (GB); Sasa Grbic, Princeton, NJ (US); Razvan Ioan Ionasec, Nuremberg (DE); Matthias John, Nuremberg (DE); Dorin Comaniciu, Princeton Junction, NJ (US)

(72) Inventors: Peter Mountney, London (GB); Sasa Grbic, Princeton, NJ (US); Razvan Ioan Ionasec, Nuremberg (DE); Matthias John, Nuremberg (DE); Dorin Comaniciu, Princeton Junction, NJ (US)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 14/970,189

(22) Filed: Dec. 15, 2015

(65) Prior Publication Data

US 2016/0180521 A1    Jun. 23, 2016

Related U.S. Application Data

(62) Division of application No. 13/775,374, filed on Feb. 25, 2013, now Pat. No. 9,247,880.

(Continued)

(51) Int. Cl.
*G06K 9/00* (2006.01)
*A61B 8/08* (2006.01)
(Continued)

(52) U.S. Cl.
CPC .......... *A61B 8/5261* (2013.01); *A61B 5/0035* (2013.01); *A61B 6/12* (2013.01); *A61B 6/4441* (2013.01); *A61B 6/487* (2013.01); *A61B 6/503* (2013.01); *A61B 6/5235* (2013.01); *A61B 6/5247* (2013.01); *A61B 8/0883* (2013.01); *A61B 8/12* (2013.01); *G06K 9/52* (2013.01); *G06K 9/6267* (2013.01); *G06T 3/0056* (2013.01); *G06T 5/50* (2013.01); *G06T 7/0028* (2013.01); *G06T 7/0034* (2013.01); *G06T 7/0048* (2013.01); *A61B 6/032* (2013.01); *A61B 6/582* (2013.01); *G06T 2207/10121* (2013.01); *G06T 2207/10132* (2013.01); *G06T 2207/20076* (2013.01); *G06T 2207/20081* (2013.01); *G06T 2207/20221* (2013.01);
(Continued)

(58) Field of Classification Search
None
See application file for complete search history.

(56) References Cited

U.S. PATENT DOCUMENTS

| | | | |
|---|---|---|---|
| 2008/0095421 A1* | 4/2008 | Sun | A61B 6/12 382/131 |
| 2008/0283771 A1* | 11/2008 | Li | A61B 6/463 250/459.1 |
| 2012/0296202 A1* | 11/2012 | Mountney | A61B 6/12 600/424 |

* cited by examiner

*Primary Examiner* — Shefali Goradia

(57) ABSTRACT

A method for real-time fusion of a 2D cardiac ultrasound image with a 2D cardiac fluoroscopic image includes acquiring real time synchronized US and fluoroscopic images, detecting a surface contour of an aortic valve in the 2D cardiac ultrasound (US) image relative to an US probe, detecting a pose of the US probe in the 2D cardiac fluoroscopic image, and using pose parameters of the US probe to transform the surface contour of the aortic valve from the 2D cardiac US image to the 2D cardiac fluoroscopic image.

16 Claims, 14 Drawing Sheets

Related U.S. Application Data

(60) Provisional application No. 61/602,107, filed on Feb. 23, 2012, provisional application No. 61/605,566, filed on Mar. 1, 2012, provisional application No. 61/605,573, filed on Mar. 1, 2012.

(51) Int. Cl.
| | |
|---|---|
| *G06K 9/52* | (2006.01) |
| *G06T 3/00* | (2006.01) |
| *G06K 9/62* | (2006.01) |
| *A61B 6/00* | (2006.01) |
| *A61B 6/12* | (2006.01) |
| *A61B 8/12* | (2006.01) |
| *G06T 5/50* | (2006.01) |
| *G06T 7/00* | (2017.01) |
| *A61B 5/00* | (2006.01) |
| *A61B 6/03* | (2006.01) |

(52) U.S. Cl.
CPC ............... *G06T 2207/30048* (2013.01); *G06T 2207/30056* (2013.01); *G06T 2207/30101* (2013.01)

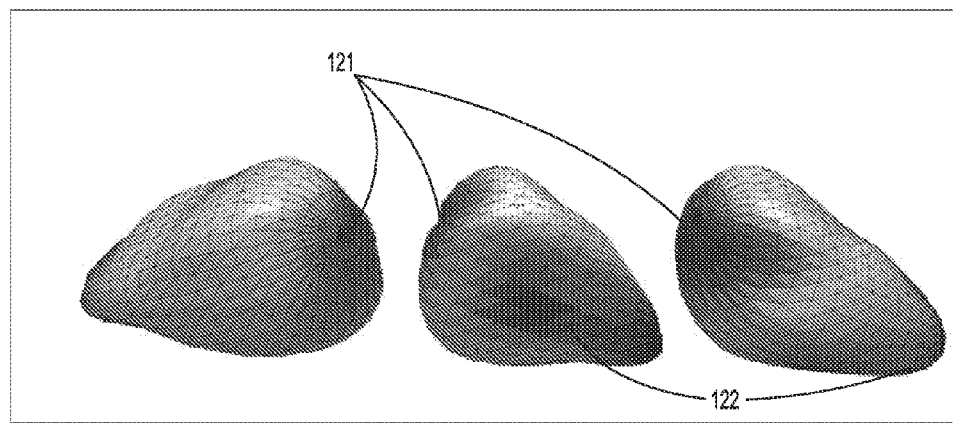
FIG. 12
| Table I | | | |
|---|---|---|---|
| | Average Error | | |
| Data | u(mm) | v(mm) | Yaw(deg) |
| Synthetic | 1.1(1.1) | 2.2(3.9) | 2.6(3.2) |
| Phantom | 1.6(1.4) | 2.0(1.2) | 3.0(3.4) |
| *In Vivo* | 2.2(5.1) | 3.7(8.0) | 6.6(16.7) |
FIG. 13
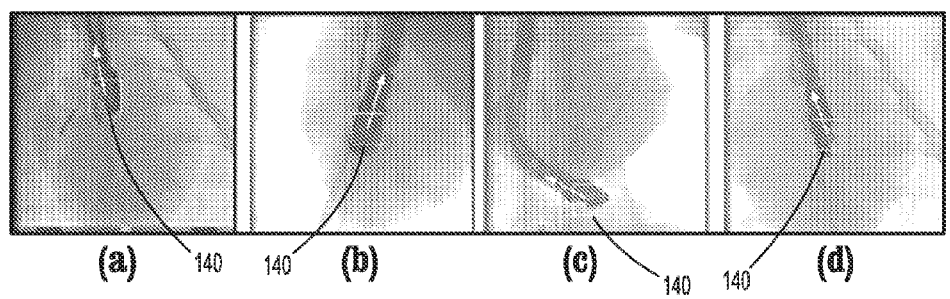
FIG. 14

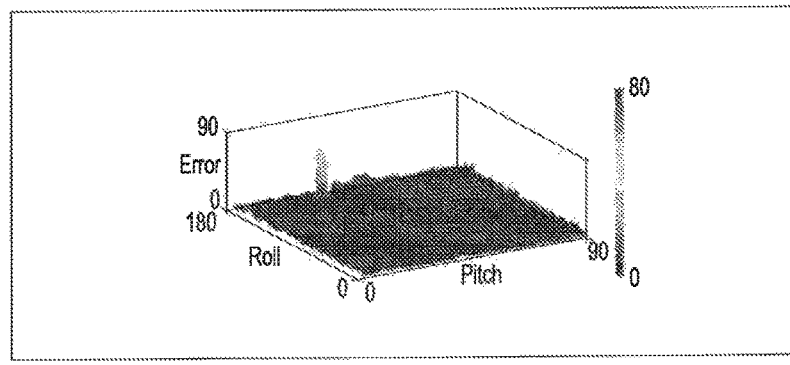
FIG. 15
Table 2
| Data | X (mm) | Y (mm) | Error Z(mm) | Roll(deg) | Pitch(deg) | Yaw(deg) |
|---|---|---|---|---|---|---|
| Synthetic | 0.82(0.79) | 0.97(2.1) | 64.0(13.9) | 4.2(10.5) | 4.6(9.0) | 2.6(3.2) |
| Phantom | 1.1(0.8) | 0.7(0.6) | 19.04(1.6) | 11.5(12.0) | 11.8(9.8) | 3.0(3.4) |
FIG. 16
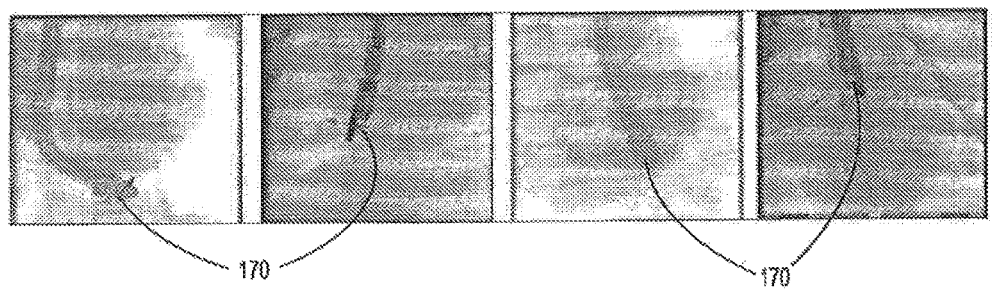
FIG. 17

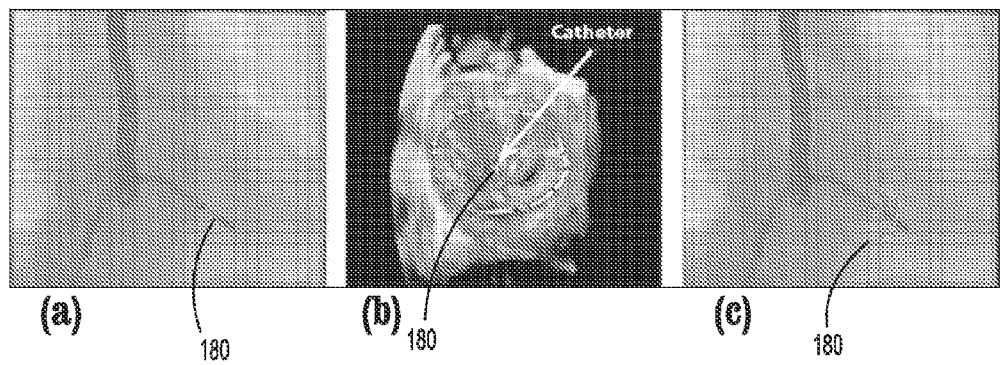
FIG. 18
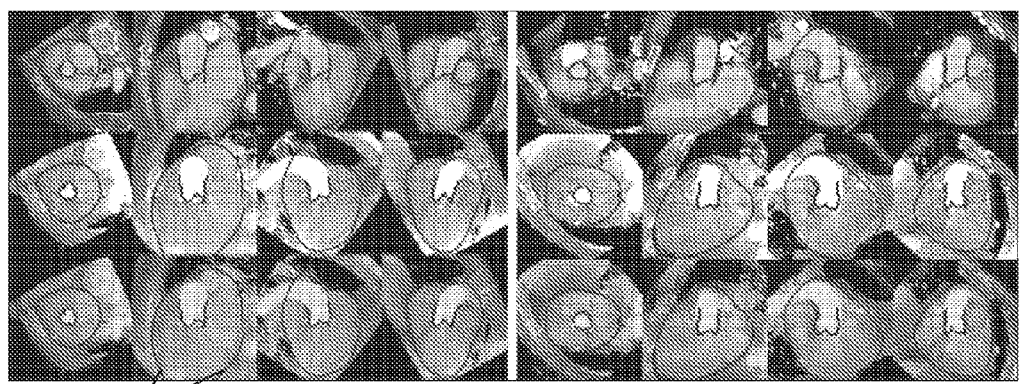
FIG. 20
Table III
|  | Mean | STD | Median |
|---|---|---|---|
| no transformation - $I$ identity matrix [mm] | 49.75 | 37.90 | 56.45 |
| rigid - registration using MI [mm] | 28.08 | 12.23 | 31.25 |
| annotation - $A_1$ and $A_2$ [mm] | 6.17 | 2.81 | 5.91 |
| our method - no prior [mm] | 5.01 | 1.90 | 4.67 |
| our method - prior [mm] | 4.04 | 0.90 | 4.18 |
FIG. 19

IMAGE FUSION FOR INTERVENTIONAL GUIDANCE

CROSS REFERENCE TO RELATED UNITED STATES APPLICATIONS

This application is a divisional of U.S. Non-provisional application Ser. No. 13/775,374 of Mountney, et al., filed Feb. 25, 2013, "Image Fusion for Interventional Guidance", which claims priority from "Real-Time TAVI Navigation: Fusing Anatomy from 2D US with Fluoroscopy", U.S. Provisional Application No. 61/602,107 of Mountney, et al., filed Feb. 23, 2012, "Robust Model-based Fusion of Pre- and Intra-Operative Images by Exploiting Data Uncertainties", U.S. Provisional Application No. 61/605,566 of Grbic, et al., filed Mar. 1, 2012, and"Ultrasound and Fluoroscopic images Fusion by Autonomous US Probe Detection", U.S. Provisional Application No. 61/605,573 of Mountney, et al., filed Mar. 1, 2012, the contents of all of which are herein incorporated by reference in their entireties.

TECHNICAL FIELD

This disclosure is directed to methods for real-time fusing of 2D and 3D images with 2D fluoroscopic images for interventional guidance.

DISCUSSION OF THE RELATED ART

Fluoroscopy guided cardiac interventions such as endovascular stenting, atrial ablation, closure of atrial/ventricular septal defects and transcatheter valve repair or replacement are proliferating. In comparison to conventional open-heart surgeries, these procedures tend to be less invasive, reduce procedural morbidity, mortality and interventional cost while accelerating patient recovery. For inoperable or high-risk patients, minimal invasive cardiac intervention is the only treatment option. However, navigating a catheter inside a patient is challenging, and without direct access or view to the affected anatomy, advanced imaging is required to secure a safe and effective execution of the procedure.

There are two established modalities currently used in operating rooms to provide real-time intra-operative images: X-ray fluoroscopy (Fluoro) and Transesophageal Echocardiography (TEE). X-ray fluoroscopy is used to visualize the catheter; however, this imaging modality does not capture soft tissue structure. Soft tissue is visualized using a second imaging modality, e.g. Transesophageal Echocardiography (TEE), or contrast agent combined with rapid pacing. Nevertheless, the splendid complementary nature of TEE and Fluoro is barely exploited in today's practice where the real-time acquisitions are not synchronized, and images are visualized separately and in misaligned coordinate systems.

On the other hand, overlays of 3D anatomical structures based on pre-operative data can provide valuable information for intervention navigation and guidance when displayed on 2D live fluoroscopy. Valuable 3D information is already routinely acquired for diagnostic and planning purposes by means of Computed Tomography, Magnetic Resonance Imaging (MRI) or Echocardiography. However, direct 3D to 2D image registration is challenge to solve, especially within the intra-operative setup that does not allow for user interaction or time consuming processing.

In a procedure such as Transcatheter Aortic Valve Implantation (TAVI), visualization of soft tissue is critical to ensure the correct placement/alignment of the implant. TEE provides useful navigation data; however, it is normal to perform rotational angiography with rapid pacing or a contrast agent to obtain models of the soft tissue structures. Overlaying rotational angiography on a fluoroscopic image enables correct alignment of the device using fluoroscopy.

However, clinical guidelines limit the duration and frequency of rapid pacing and the volume of contrast agent that can be administered to a patient, due to negative effects on the heart and kidneys. An alternative approach is to visualize soft tissue information from TEE in the fluoroscopic image. This will facilitate navigation of the implant device in fluoroscopy.

The fusion of fluoroscopic and ultrasound (US) images into a single space is challenging. Fluoroscopy is a projective imaging modality and US is 2D or 3D. These modalities are not intuitively visualized in the same space. In addition care must be taken to visualize meaningful information and to not occlude important data.

The fusion of Fluoro and TEE can be accomplished using either hardware or image-based methods. Hardware based approaches attach additional devices to the ultrasound probe, such as electromagnetic or mechanical trackers and align the device and Fluoro coordinates systems through calibration. These devices track the position and orientation of the probe in a coordinate system defined by the tracking device. Through a calibration process, the transformation between the ultrasound image and the tracked point on the probe is estimated. This transformation is rigid and does not change during the procedure. A second calibration procedure estimates the transformation between the tracking device coordinate system and the X-ray fluoroscopy device. Concatenating these transformations registers the ultrasound image into the X-ray fluoroscopy image. It is assumed that the ultrasound image is not rotated or zoomed.

The introduction of additional hardware into the already crowded operating theatre is not desirable, as it can require time consuming configuration and may be disruptive to the workflow. In additional, electromagnetic tracks can suffer from noise and interference leading to inaccuracies.

Image based methods attempt to use the appearance of the TEE probe in the Fluoro image to estimate the pose of the probe in the fluoroscopic coordinate system. Image based methods are attractive because they do not require the introduction of additional equipment into the theatre which may disrupt clinical workflow. Image based pose estimation is well studied and may be considered solved when the correspondence between 2D image points and a 3D model are known. Unfortunately, the appearance of the TEE probe in the Fluoro image makes establishing the correspondence challenging. The probe's appearance lacks texture or clear feature points and can be homogenous under low dose or close to dense tissue.

C-arm CT is emerging as a novel imaging modality that can acquire 3D CT-like volumes directly in the operating room, in the same coordinate space as the 2D live fluoroscopy images, which overcomes the need for 2D/3D registration. Some methods work directly on the 3D C-arm CT images to extract patient specific models and overlays for procedure guidance, eliminating the need for pre- and intra-operative image fusion completely. However, performing high-quality, contrasted, and motion compensated (using rapid-pacing) C-arm CT images is not feasible for all patients. Instead, a much simpler protocol, which acquires non-contrasted, non-ECG-gated C-arm CT volumes, can be performed to serve as a bridge between 3D pre-operative images and 2D live fluoroscopy. Multi-modal 3D-3D registration algorithms can be utilized to align the pre-operative image with the C-arm CT volume. FIG. 1 depicts several fused images of an intra-operative 3D C-arm CT overlaid with pre-operative model of the aortic valve extracted from CT. The CT is indicated by reference number 11 while an overlaid aligned native rotational angiography is indicated by reference number 12. However, existing methods are computationally expensive, and without the appropriate guidance of a shape prior are unlikely to converge to local minima.

SUMMARY

Exemplary embodiments of the invention as described herein generally include methods for fusing 3D pre-operative anatomical information with live 2D intra-operative fluoroscopy via non-contrasted 3D C-arm CT. Embodiments employ robust learning-based methods to automatically extract patient-specific models of both target and anchor anatomies from CT. Anchor anatomies have correspondences in the pre-operative and intra-operative images while target anatomies are not visible in the intra-operative image but are essential to the procedure. A sparse matching approach is employed to align the pre-operative anchor anatomies to the intra-operative setting. Data and model uncertainties are learned and exploited during the matching process. A method according to an embodiment of the invention can cope with artifacts in the intra-operative images, partially visible models and does not require contrast agent in the intra-operative image.

Further exemplary embodiments of the invention as described herein generally include methods for a robust and fast learning-based method for the automated detection and visualization of the TEE probe pose, with six degrees of freedom, from Fluoro images. Embodiments employ a probabilistic model-based approach to estimate candidates for the in-plane probe position, orientation and scale parameters, and digitally reconstructed radiography (DRR) in combination with a fast matching based on binary template representation for the estimation of out-plane rotation parameters (pitch and roll). An approach according to an embodiment of the invention is an image only approach which requires no additional hardware to be incorporated into the operating theatre, does not require manual initialization, is robust over the entire pose parameter space, and is independent of specific TEE probe design/manufacturer. The 6 degree-of-freedom (DoF) pose of the probe can be detected from 2D fluoroscopy enabling the ultrasound (US) fan to be visualized in the same coordinate system as the fluoroscopy.

Further exemplary embodiments of the invention as described herein generally include methods for visualizing high contrast information extracted from the US of anatomically significant structures, specifically the aortic root and leaflets, to facilitate implant guidance, and the pose of the US probe in the fluoroscopic image. Embodiments can meet real time requirements by detecting critical soft tissue anatomy in 2D US images.

According to an aspect of the invention, there is provided a method for real-time fusion of a 2D cardiac ultrasound image with a 2D cardiac fluoroscopic image, including detecting a surface contour of an aortic valve in the 2D cardiac ultrasound (US) image relative to an US probe, detecting a pose of the US probe in the 2D cardiac fluoroscopic image, and using pose parameters of the US probe to transform the surface contour of the aortic valve from the 2D cardiac US image to the 2D cardiac fluoroscopic image.

According to a further aspect of the invention, detecting the surface contour of the aortic valve includes modeling a global location of the aortic valve by a bounding box with a specified center and orientation, where the global location includes a center position, an orientation and a scale of the aortic valve, locating anatomical landmarks of the aortic valve, including 2 landmarks on the aortic valve annulus and 2 landmarks on the aortic valve commissure plane, and modeling the aortic valve borders with a first contour and a second contour, the first and seconds contours being constrained by the aortic valve annulus landmarks and the aortic valve commissure plane landmarks.

According to a further aspect of the invention, the method includes detecting the global position, anatomical landmarks, and first and second contours are using marginal space learning with a hierarchical approach, where detectors are successively trained using probabilistic boosting trees.

According to a further aspect of the invention, the method includes finding an optimal imaging angle for the US probe by rotating the US probe about its axis, and detecting an angulation of an US fan with respect to the aortic root, and selecting a probe orientation that maximizes the angulation of the US fan with respect to the aortic root as the optimal imaging angle.

According to a further aspect of the invention, the method includes inserting the US image into the fluoroscopic image.

According to a further aspect of the invention, detecting a pose of the US probe in the 2D cardiac fluoroscopic image includes determining a position (u,v), orientation ($\theta y$), and size (s) of an ultrasound (US) probe in a fluoroscopic image, determining a roll and pitch of the US probe in the fluoroscopic image, where the position, orientation, size, roll and pitch comprise pose parameters of the probe, and using the probe pose parameters to transform points in the 2D cardiac ultrasound image into the 2D cardiac fluoroscopic image, where the 2D cardiac ultrasound image is visualized in the 2D cardiac fluoroscopic image.

According to a further aspect of the invention, determining the position, orientation, and size of the US probe in the fluoroscopic image comprises sequentially applying a classifier for each of the position, orientation, and size, respectively, where each classifier is trained using a probabilistic boosting tree.

According to a further aspect of the invention, each of the classifiers is trained using Haar-like features.

According to a further aspect of the invention, determining the position of the US probe comprises applying a steerable filter to the 2D fluoroscopic image to identify regions of high contrast which are likely to contain the US probe.

According to a further aspect of the invention, determining the size of the US probe comprises detecting two points where a tip of the probe meets a shaft of the probe, where the orientation and position of the US probe are used to constrain a search area for the size detector.

According to a further aspect of the invention, determining the roll and pitch of the US probe in the fluoroscopic image comprises matching an image patch of the fluoroscopic image containing the US probe with each of a plurality of image templates, where each image template is associated with a particular combination of roll and pitch values, where the pitch and roll of a template that best matches the image patch are selected as the roll and pitch of the US probe.

According to another aspect of the invention, there is provided a method of transforming target structure anatomies in a pre-operative image $I_2$ into an intra-operative image $I_1$, including determining a transformation $\Phi$ aligns a target structure $T_2$ and an anchor structure $A_2$ in the pre-operative image $I_2$ into a corresponding target structure $T_1$ and anchor structure $A_1$ in the intra-operative image $I_1$ by finding a transformation $\hat{\Phi}$ that maximizes a functional $\log(P(\Phi|I_1,A_2))$ using an expectation-maximization approach, where the target structure $T_1$ is not visible in the intra-operative image.

According to a further aspect of the invention, the transformation $\Phi$ is a rigid transformation, where an initial transformation $\Phi^0$ is approximated as a translation, where $\Phi^0$ represents a translation between a barycenter $a_2$ of the anchor anatomy $A_2$ in the pre-operative image $I_2$ and a detected barycenter $a_1$ of the anchor anatomy $A_1$ in the intra-operative image $I_1$.

According to a further aspect of the invention, the initial transformation $\Phi^0$ is determined by a position detector trained by a probabilistic boosting tree classifier and Haar features on the barycenter $a_1$ of the anchor anatomy $A_1$ in the intra-operative image $I_1$.

According to a further aspect of the invention, the pericardium is used as the anchor anatomy $A_1$ and $A_2$ and the aortic valve is used as the target anatomy $T_1$ and $T_2$.

According to a further aspect of the invention, finding a transformation $\hat{\Phi}$ that maximizes a functional $\log(P(\Phi|I_1,A_2))$ includes generating K sample $\Phi_i^t$ point sets $(x_1, x_2, x_3, \ldots, x_K)$ from the pre-operative anchor anatomy $A_2$, where each point set comprises N points and each sample is represented as an isotropic 6D Gaussian distribution $\Phi_i^t=N_6(\mu_i,\Sigma_i)$, $\Sigma_i=\sigma_i I$, where I is an identity matrix and $\sigma_i$ is a one dimensional variable calculated as a kernel function from a probability map $F(I)$ evaluated at the point locations $y_{i,j}$, $i=1, \ldots, K$, $j=1, \ldots, N$, transforming the point sets $\Phi_i^t$ into the intra-operative image $I_1$ locations $y^*_i=\Phi^t(x_i)$, $i=1, \ldots, K$, according to an appearance of the intra-operative image $I_1$, assigning each point $y^*_{i,j}$, $j=1, \ldots, N$ from the point set $x_i$ to a new location $y_{i,j}$, $j=1, \ldots, N$, based on a local appearance of the intra-operative image $I_1$, approximating final parameters of each sample $\Phi_i^t$ by an isotropic Gaussian distribution, where a mean $\mu$ is computed from a least squares solution between the point set $\Phi_i^t$ in the pre-operative $I_2$ and the updated point set $(y_1, y_2, y_3, \ldots, y_K)$ in the intra-operative image $I_1$ by minimizing the mapping error function $$e_i = \frac{1}{N}\sum_{j=1}^{N} \|\Phi_i^t(x_{i,j}) - y_{i,j}\|,$$

and determining an updated global transformation $\Phi^{t+1}$ from $$\Phi^{t+1} = \underset{\Phi}{\mathrm{argmax}}(\Phi \mid \Phi^t)$$

based on an estimated mixture model $$\oplus = \sum_{i=1}^{K} \Phi_i^t$$

of the K transformation samples $\Phi_i^t$, $i=1, \ldots, K$.

According to a further aspect of the invention, $$\Phi^{t+1} = \underset{\Phi}{\mathrm{argmax}}(\Phi \mid \Phi^t)$$

is estimated using a mean shift algorithm.

According to a further aspect of the invention, the method includes deriving the probability map $F(I_1)$ from the intra-operative image $I_1$ by evaluating a boosting classifier trained using Haar features and surface annotations of the anchor anatomy $A_1$ in the intra-operative image $I_1$, where each vertex of a model of the intra-operative image $I_1$ is assigned as a positive sample and random points within a threshold distance are used as negative samples, and those vertices for which a feature response is low are rejected as positive examples.

According to a further aspect of the invention, minimizing the mapping error further comprises estimating a prior probability for each vertex of a model of pre-operative image $I_2$ by assigning each vertex of a model of the pre-operative image $I_2$ as a positive sample and using random points within a threshold distance as negative samples, rejecting those vertices for which a feature response is low as positive examples, estimating a ground-truth mapping $\Phi_T$ based on hinges and commissures of the aortic valve, and transforming each intra-operative model of the pre-operative anchor anatomy $T_2$ into the pre-operative image $I_1$ using $T^*_1=\Phi_T T_2$ and the variance of a point-wise distance $\|T^*_1-T_1\|$.

According to another aspect of the invention, there is provided a non-transitory program storage device readable by a computer, tangibly embodying a program of instructions executed by the computer to perform the method steps for transforming target structure anatomies in a pre-operative image $I_2$ into an intra-operative image $I_1$.

BRIEF DESCRIPTION OF THE DRAWINGS

FIG. 12 illustrates prior weights indicating the significance of each vertex for an accurate mapping with respect to the aortic valve according to an embodiment of the invention.

FIG. 13 is a table showing quantitative validation of the in-plane position and orientation parameters for three datasets, according to an embodiment of the invention.

FIGS. 14(a)-(d) are fluoroscopic images illustrating probe detection and the estimation of in-plane parameters from in vivo images, according to an embodiment of the invention.

FIG. 15 plots the (θr, θp) error in mm over the search space in degrees, according to an embodiment of the invention.

FIG. 16 is a table of the quantitative validation results for TEE probe detection, according to an embodiment of the invention.

FIG. 17 depicts detection examples of the probe pose in in vivo images, according to an embodiment of the invention.

FIGS. 18(a)-(c) illustrate an anatomical mitral valve model detected in 3D TEE and visualized in Fluoro, according to an embodiment of the invention.

FIG. 19 is a table of the mean, median and standard deviations of various transformations, according to an embodiment of the invention.

FIG. 20 shows several examples of fused volumes with a mapped aortic valve model detected in a pre-operative CT image mapped into a non-contrasted intra-operative 3D C-arm CT image using a sparse matching method with prior sampling according to an embodiment of the invention.

DETAILED DESCRIPTION OF EXEMPLARY EMBODIMENTS

Figure 1:
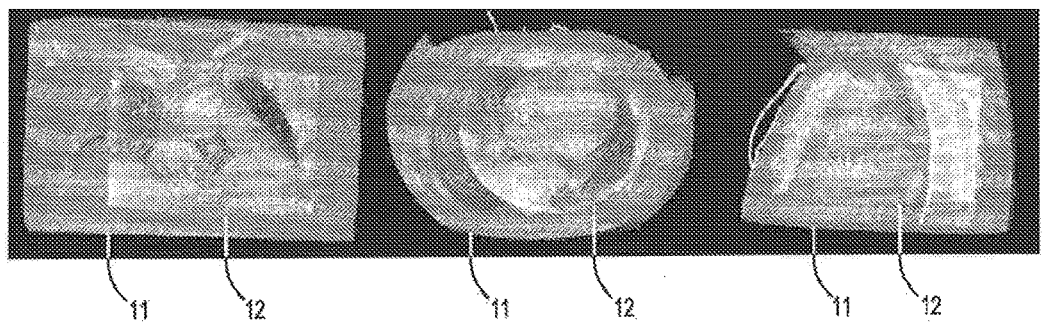
FIG. 1 depicts several fused images of an intra-operative 3D C-arm CT overlaid with pre-operative model of the aortic valve extracted from CT, according to an embodiment of the invention.

Exemplary embodiments of the invention as described herein generally include systems and methods for fusing images for interventional guidance. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Methods

Figure 2:
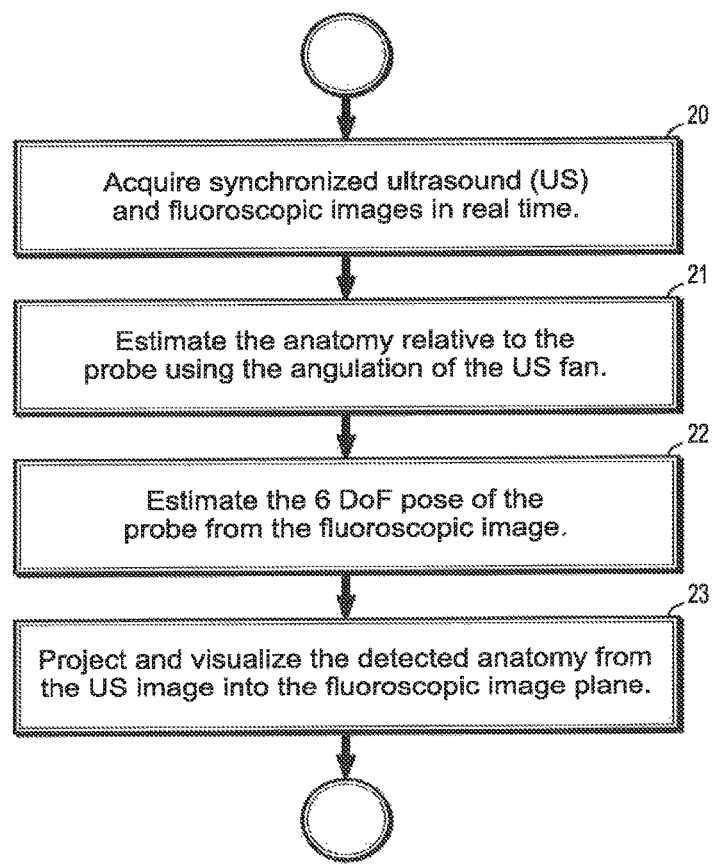
FIG. 2 is flowchart of a method for real time image fusion according to an embodiment of the invention.
Figure 3:
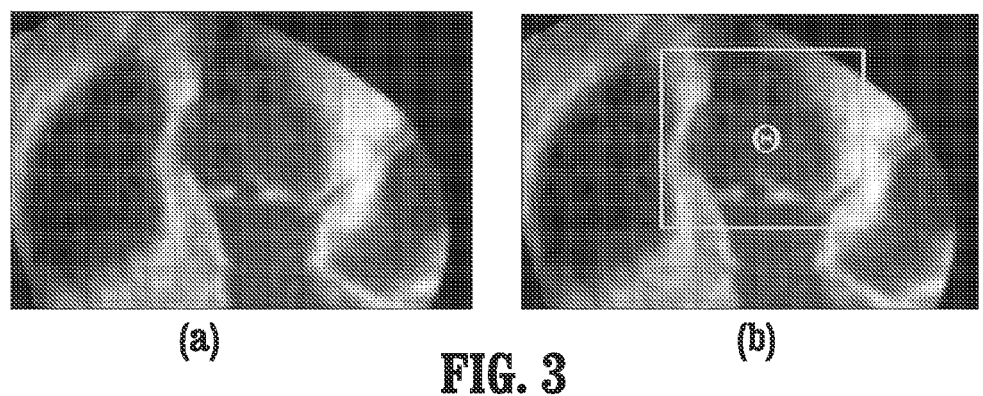
FIGS. 3(a)-(b) depict a 2D ultrasound image of the aortic valve and a bounding box showing the global position of the aortic valve according to an embodiment of the invention.

Methods according to an embodiment of the invention can extract critical soft tissue information from 2D TEE in real time. A flow chart of a method for real time image fusion according to an embodiment of the invention is shown in FIG. 2. In a first step 20 real time synchronized US and fluoroscopic images are acquired. The 2D US image is processed to detect the aortic anatomy. The anatomy includes but is not limited to the aortic root and the leaflets. To visualize the detected anatomy in the fluoroscopic image, at step 21 the anatomy is estimated relative to the probe using the angulation of the US fan, and at step 22 the 6 DoF pose of the probe is estimated from the fluoroscopic image. Given this information and the intrinsic calibration parameters of the fluoroscopic device, the detected anatomy can be projected into the fluoroscopic image plane at step 23 and visualized. FIG. 3(a) depicts a 2D US image of the aortic valve.

Embodiments of the invention can detect the surface contour of the aortic valve in 2D (TEE) ultrasound using a multi-level hierarchical approach. On a coarsest layer, the location, orientation and scale are modeled as a bounding box θ, as shown in FIG. 3(b), where $\theta = \{c_1, c_2, \alpha\}$, where $c_1$, $c_2$ represent the x- and y-coordinates of the bounding box center and α the rotation. The size or scale of the bounding box is learned from the modeling.

Figure 4:
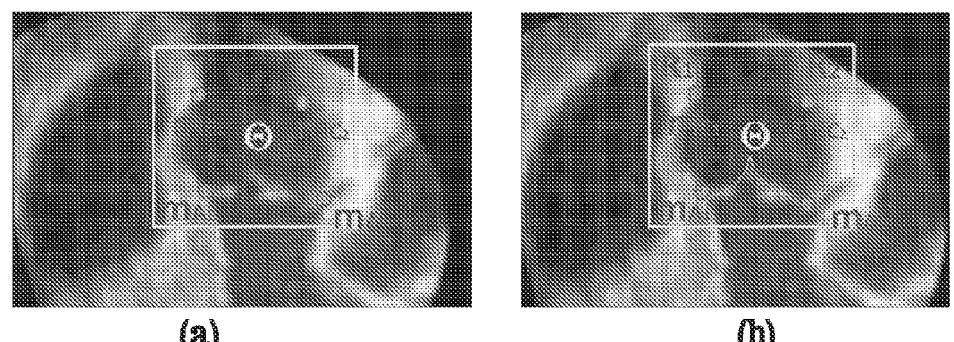
FIGS. 4(a)-(b) depict a landmark model of the aortic valve, and a complete model of the aortic valve including the contours constrained by the bounding box and the landmarks according to an embodiment of the invention.

A second modeling layer according to an embodiment of the invention includes four landmarks $(m_{A1}, m_{A2}, m_{C1}, m_{C2})$ where $m_{A1}$ and $m_{A2}$ are Located on the Aortic Valve annulus and $m_{C1}$ and $m_{C2}$ on the commissure plane. FIG. 4(a) depicts a landmark model of the aortic valve, according to an embodiment of the invention. A third modeling layer according to an embodiment of the invention includes two contours R1 and R2 which are constrained by the bounding box, annulus and commissures landmarks. FIG. 4(b) depicts a complete model of the aortic valve including the contours R1 and R2, according to an embodiment of the invention According to embodiments of the invention, patient-specific parameters of the aortic valve model can be estimated from the 2D or 2×2D (X-Plane) ultrasound images using robust learning-based algorithms that use hierarchical approaches within a Marginal Space Learning (MSL) approach. Detectors are successively trained using the Probabilistic Boosting Tree (PBT) with Haar and Steerable features, and are subsequently applied to estimate the global location θ followed by anatomical landmarks $(m_{A1}, m_{A2}, m_{C1}, m_{C2})$ and surface structures R1 and R2.

A model according to an embodiment of the invention is estimated in the ultrasound image space and can therefore be transformed into the fluoroscopic image space using the approach described above.

An approach to US probe pose estimation according to an embodiment of the invention first detects the probe in the fluoroscopic image with three degrees of freedom, two translational degrees and one rotation degree, in the image plane. According to an embodiment of the invention, the probe can be detected using Marginal Space Learning and Probabilistic Boosting trees. A classifier according to an embodiment of the invention can be trained on manually labeled data, and can extract features which distinguish positively labeled data from negatively labeled data. Embodiments use non-maximal suppression to reduce the number of candidates, and boot strapping to initialize a detection and tracking process according to an embodiment of the invention.

A pose estimation according to an embodiment of the invention has 6 DoF. According to an embodiment of the invention, the remaining 3 degrees of freedom can be estimated using a second classifier. The second classifier can be trained to estimate the Z translation (depth), pitch and roll of the probe. The classifier is trained on synthetically generated training data where the ground truth position of the probe is known. According to an embodiment of the invention, a filter such as an Extended Kalman or a Particle filter can be used to exploit temporal information between frames, which reduces the search space, enabling the pose of the probe to be predicted.

A new clinical workflow according to an embodiment of the invention can determine an optimal US orientation for visualization of the aortic root. Detection of the aortic root in 2D US is beneficial for real time computation, however, the detected segments are only a partial representation of the root. To visualize the whole root structure, an operator can move the US device and determine an optimal imaging plane for visualization of the aortic structures in fluoroscopy. An optimal imaging angle is one which visualizes a widest point of the aortic root and thus facilitates implantation of a prosthetic device.

Figure 5:
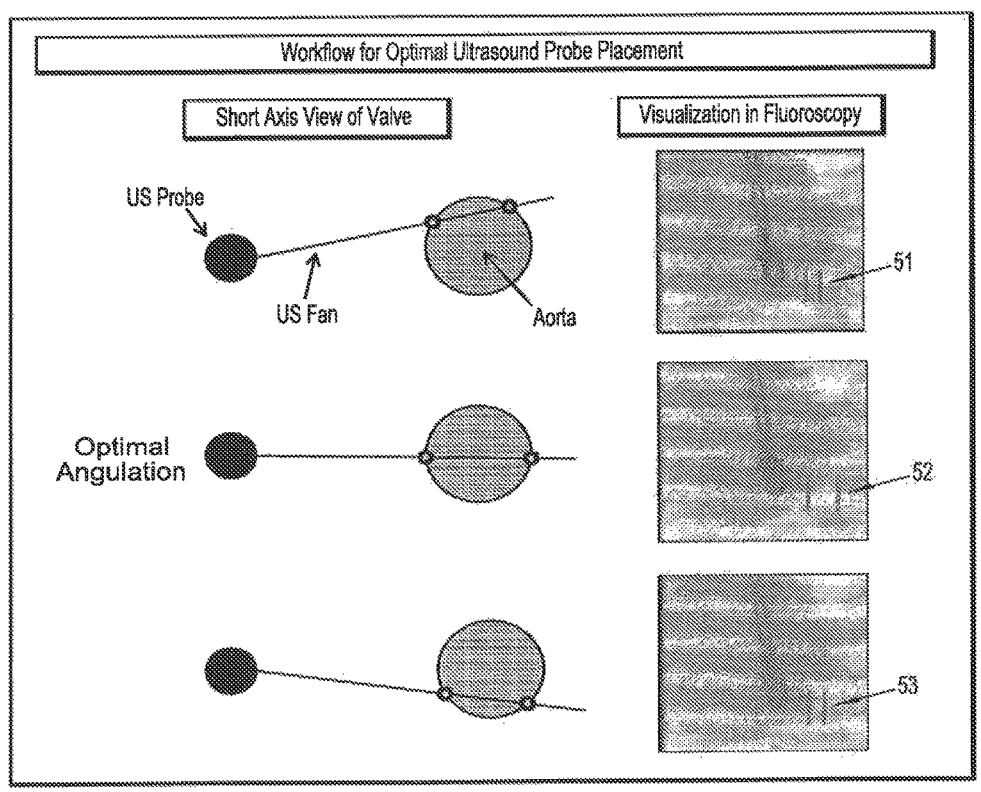
FIG. 5 is a schematic visualization of an optimization process according to an embodiment of the invention.

FIG. 5 is a schematic visualization of an optimization process according to an embodiment of the invention. This figure represents a simple case in which the US probe is rotated around its axis, changing the angulations of the US fan with respect to the aortic root. Three steps of a continuous motion are shown in FIG. 5. The user starts with an initial visualization in fluoroscopy 51 of the aortic root represented by two lines. At this point it would not be clear to the operator if this is an optimal visualization, i.e., the widest point of the aortic root. By rotating the probe around the axis, as shown on the left side of FIG. 5, the operator can see the lines move further apart 52 as an optimal visualization plane is approached. These lines will then move back together 53 after passing the optimum visualization plane. Through guided navigation and exploration the operator can determine the optimal imaging plane.

It should be noted that the aortic anatomy may not always be visualized as straight or parallel lines. The visualization is dependent on the 6 DoF orientation of the US probe and the shape of the anatomy. This does not affect the effectiveness of the navigation or the usefulness of the visualization to assist in determining an optimal orientation of the US probe, as it is still possible to visualize the widest part of the aortic root.

Figure 6:
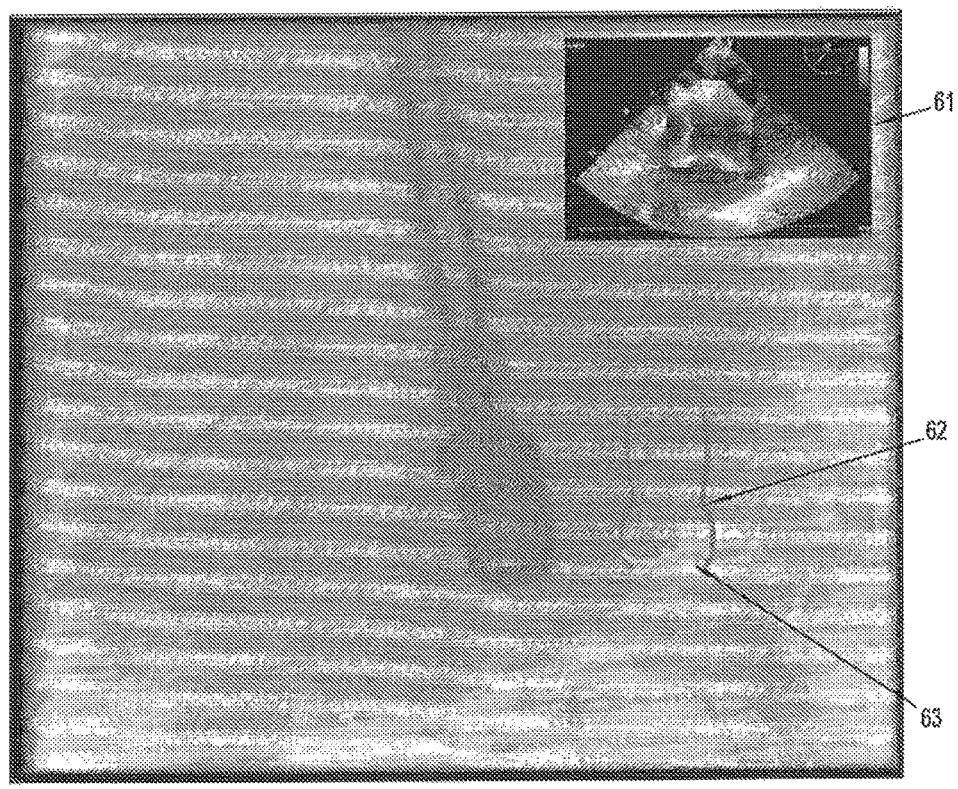
FIG. 6 depicts an example of a picture-in-picture visualization, according to an embodiment of the invention.

According to an embodiment of the invention, a picture-in-picture visualization can enable a physician to verify the correctness of the detected anatomy, and to verify that models visualized in the fluoro correspond to that in the TEE. FIG. 6 depicts an example of a picture-in-picture visualization, according to an embodiment of the invention, with US picture 61 embedded in the upper right corner of the image. FIG. 6 also depicts the aortic root 62 and the aortic valve 63.

A method of fusing 2D TEE images with 2D fluoroscopic images can reduce the need for rapid pacing, reduce the use of a contrast agent, decrease procedure times, guide an ultrasound operator to find an optimal imaging plane, and provide a clear visualization of anatomy, by overlaying a TEE image on a fluoroscopic image.

According to another embodiment of the invention, information from a TEE volume can be visualized in a fluoroscopic image by aligning the TEE and C-arm fluoroscopic coordinate systems. A point $Q^{TEE}$ in an ultrasound volume can be visualized in a fluoroscopic image at coordinate (u, v)=$Q^{Fluoro}$ using a following transformation, according to an embodiment of the invention:

$$Q_{Flouro} = P_{Projection} R_{xz} T_d R_\gamma R_\alpha (R_{TEE}^W Q^{TEE} + T_{TEE}^W) \qquad (1)$$

where $P_{Projection}$ is a projection matrix, $R_{xz}$ and $T_d$ are the transformations from a detector to a world coordinate system, $R_\gamma$ and $R_\alpha$ are the angulations of the C-arm, and $R_{TEE}^W$ and $T_{TEE}^W$ are the rotation and position of the TEE probe in a world coordinate system such that $R_{TEE}^W = R_\alpha^{-1} R_\gamma^{-1} R_{xz}^{-1} R_{TEE}^{Fluoro}$ and $T_{TEE}^W = R_\alpha^{-1} R_\gamma^{-1} T_d^{-1} R_{xz}^{-1} T_{TEE}^{Fluoro}$. The TEE volume and fluoroscopic image can be aligned if position $T_{TEE}^{Fluoro} = (x,y,z)$ and orientation $R_{TEE}^{Fluoro} = (\theta r, \theta p, \theta y)$ of the TEE probe in the Fluoroscopic detector coordinates.

Figure 7:
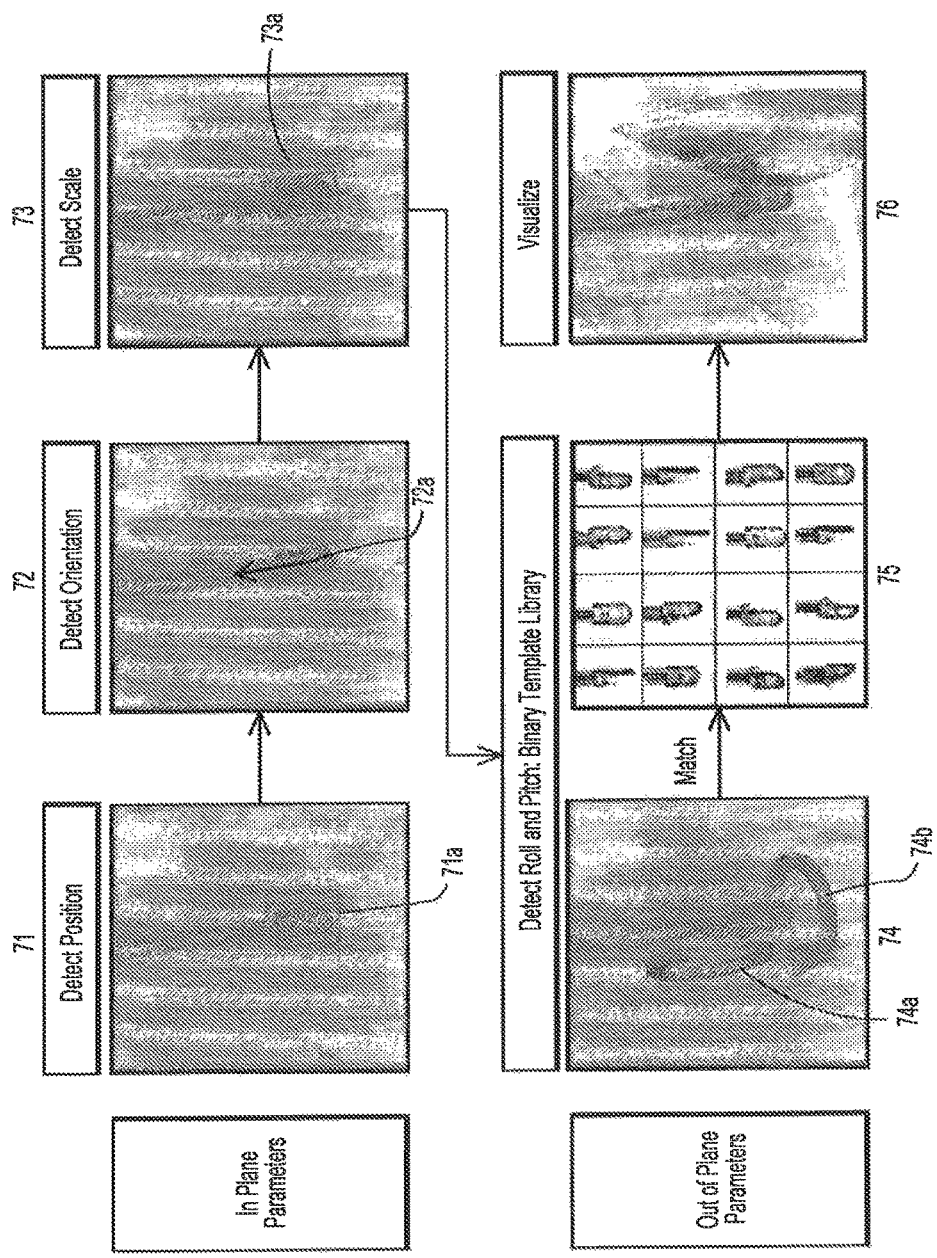
FIG. 7 shows a framework for determining in-plane and out-plane parameters, according to an embodiment of the invention.

An approach according to an embodiment of the invention separates the pose parameters into in-plane (x, y, z) and (θy) parameters and out-plane (θr, θp) parameters. By marginalizing the estimation, embodiments can efficiently estimate in-plane parameters directly from the Fluoro images, while being invariant against the out-plane parameters that are more challenging to determine. A framework according to an embodiment of the invention for determining in-plane and out-plane parameters is illustrated in FIG. 7.

According to an embodiment of the invention, the in-plane parameters can be computed from the position (u, v), size (s) and orientation (θy), given a projection transformation P of the calibration information of the fluoroscopic device and the physical dimensions of the TEE probe. Embodiments of the invention can detect the in-plane parameters (u, v), (s), (θy) from a Fluoro image using discriminative learning methods described below.

According to an embodiment of the invention, to estimate the in-plane parameters, discriminative learning methods can be used to train a classifier that detects the position (u, v), the orientation (θy), and the size (s) of the TEE probe in the Fluoro image. Three classifiers can be trained using manually annotated Fluoro data. According to an embodiment of the invention, the classifiers are trained and sequentially applied so that first, candidates 71a are detected for (u, v) at step 71, then the orientation (θy) 72a is detected for each candidate at step 72, and finally the size 73a of the probe is detected (s) at step 73.

Each detector is a Probabilistic Boosting Tree (PBT), a binary classifier. According to an embodiment of the invention, each detector is trained using Haar-like and steerable features. A position (u, v) detector according to an embodiment of the invention is trained on manual annotations and negative examples randomly extracted to from the fluoroscopic image. An exemplary, non-limiting fluoroscopic image is resized to 128×128 and a 35×35 window is centered at the annotation. 100,000 Haar features are used to train the PBT. The appearance of the probe varies greatly and to avoid over fitting, embodiments create a classifier which is less discriminative but more likely to detect the tip of the probe. During detection a steerable filter is applied to the image to identify regions of high contrast which are likely to contain the TEE probe. This reduces the number of image patches to be classified by the probe and improves speed.

An orientation (θy) detector according to an embodiment of the invention is trained on manually annotated data and the false positives from the position detector. Additional negative training data is created centered on the annotation but with incorrect rotation parameters. A PBT according to an embodiment of the invention can be trained with five features, including the relative intensity and the difference between two steerable filters applied to the image with different parameters. An orientation detector according to an embodiment of the invention is trained at intervals of six degrees with a 360 degree coverage. An orientation detector according to an embodiment of the invention is more discriminative than the position detector and therefore can remove outliers as well as estimating the orientation.

A size (s) detector according to an embodiment of the invention is trained to detect two points where the tip of the probe meets the shaft. This part of the probe is circular and appears the same size invariant of the pose. A PBT according to an embodiment of the invention can be trained using Haar features. During detection the orientation and position of the probe are used to constrain the search area for the size detector.

The out-plane parameters are more challenging to estimate. The appearance of the probe under roll and pitch (θr, θp) varies significantly in the fluoroscopic image and cannot generally be accounted for in the image space using the same techniques as used for the in plane parameters, making it challenging to train a compact classifier. Embodiments of the invention take a different approach by creating a template library of fluoroscopic images of the probe under different out-of-plane orientations (θr, θp). Referring again to FIG. 7, at step 74, the (θr, θp) parameters 74a, 74b are estimated by matching an image patch, normalized for the in-plane parameters, with the template library. Each template has an associated (θr, θp) and by matching the fluoroscopic image to the template at step 75 one can estimate the out-of-plane parameters as below. The TEE probe can be visualized at step 76.

A template library according to an embodiment of the invention should contain a wide variety of orientations. It is not feasible to build this library from in vivo data as it is challenging to manually annotate (θr, θp) and the data may not be comprehensive. Embodiments build a library using Digitally Reconstructed Radiography (DRR). DRR's can simulate X-ray fluoroscopy by tracing light rays through a 3D volume. For this purpose, a 512×512×433 rotational angiography of the TEE probe is acquired with a 0.2225 mm resolution. The orientation and position of the probe is manually annotated and (θr, θp) orientations are applied to the volume. Generating DRR images is computationally expensive and moving this stage offline saves computation online.

Searching a template library according to an embodiment of the invention can be computationally expensive. The size of the library can be limited to reduce the search space. The probe is not free to move in all directions due to physical constraints of the tissue. In addition, the X-ray image is an integral image and is therefore reflective. These two facts can be exploited by embodiments to reduce the size of the template library. According to an embodiment of the invention, a library was built with pitch poses from −45 to 45 degrees and roll poses from −90 to 90 degrees with two degree intervals. The library includes 4050 image patches. These values are exemplary and non-limiting, and template libraries can be built over different angular ranges with different angular intervals in other embodiments of the invention.

This subsample library is still large and expensive to store and search. To make searching computationally tractable, embodiments use a binary template representation. Binary templates are an efficient way of storing information about an image patch which can be useful for matching. In addition because the information is stored in binary, matching can be quickly performed using bitwise operations.

Figure 22:
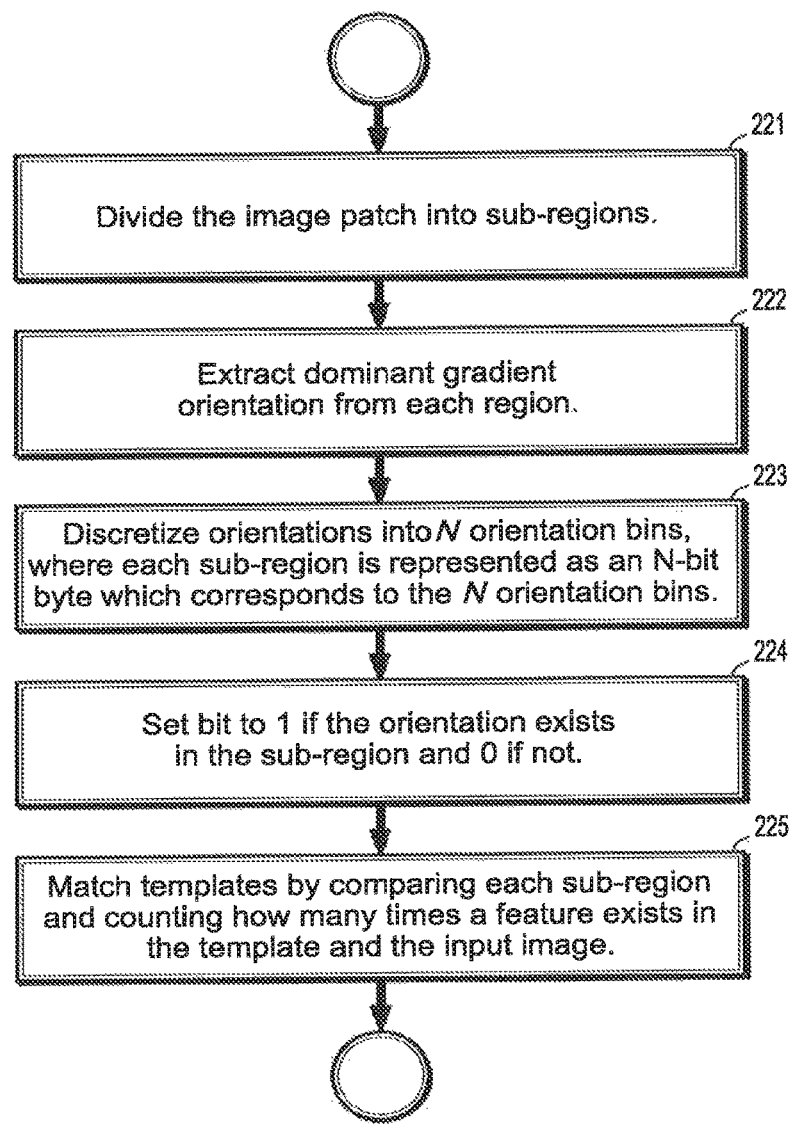
FIG. 22 is a flowchart of a method of matching an image patch with the image templates in the template library, according to an embodiment of the invention.

A flowchart of a method according to an embodiment of the invention of matching an image patch with the image templates in the template library is presented in FIG. 22. Referring now to the figure, the image patch can be divided into sub-regions at step 221 and features can be extracted from each region at step 222. The dominant gradient orientation in each subregion is taken to be a feature, which works well on homogenous regions and objects which lack texture, as is the case for a TEE probe in the fluoroscopic image. The orientations can be discretized into N orientation bins at step 223. Each sub-region can be represented as an N-bit byte which corresponds to the N orientation bins. An exemplary, non-limiting value for N is 8. At step 224, the bit is set to 1 if the orientation exists in the sub-region and 0 if it does not. The binary template for the image patch is comprised of a set of bytes corresponding to the sub-regions. The resulting template is a compact and discriminative representation of the image patch.

According to an embodiment of the invention, templates are matched at step 225 by comparing each sub-region and counting how many times a feature exists in the template and the input image. There is no measurement of the similarity of the features, only that a feature exists in a sub-region. The similarity measure is $$\varepsilon(I^{Fluoro}, O, c) = \sum_r \delta(F(I^{Fluoro}(u, v) + r) = F(O, r)), \qquad (2)$$

where δ(P) is a binary function which returns true if two features match, $F(I^{Fluoro}(u,v)+r)$ is the input template centered on candidate (u,v) in image $I^{Fluoro}$ and F(O, r) is a template from the template library. This function can be evaluated very quickly using a bitwise AND operation followed by a bit count. The final matching score is the bit count and the (θr, θp) associated with the highest matching template is used to estimate the out-of-plane parameters.

According to another embodiment of the invention, a transformation Φ between the target structure anatomies $T_1$ and $A_1$ in an intra-operative image $I_1$, and source structure anatomies $T_2$ and $A_2$ in a pre-operative image $I_2$ can be estimated:

$$(T_1) = \Phi(T_2, A_2). \qquad (3)$$

Figure 8:
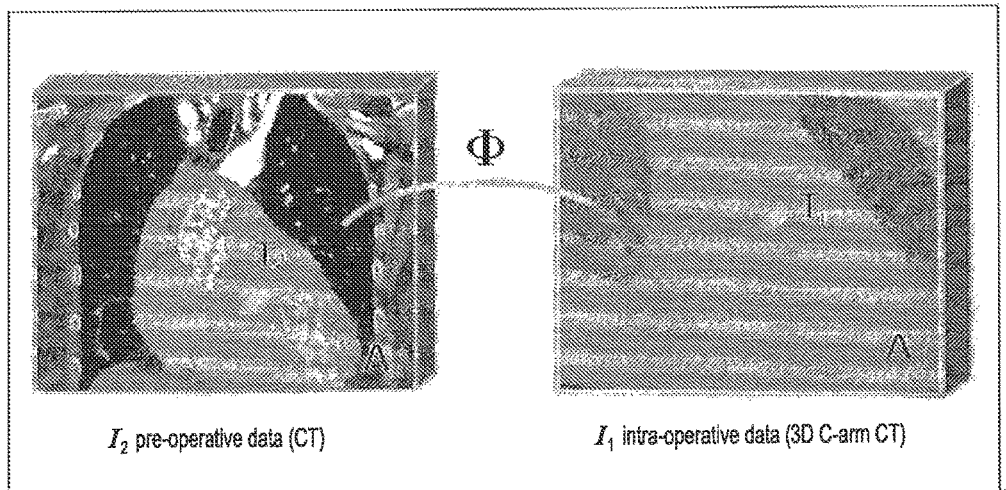
FIG. 8 illustrates a formulation of fusing a pre-operative CT image into an intra-operative 3D C-arm CT image, according to an embodiment of the invention.

FIG. 8 illustrates a fusion formulation according to an embodiment of the invention, showing the target $T_1$ and $T_2$ and anchor $A_1$ and $A_2$ anatomies. The transformation matrix c maps the pre-operative CT image $I_1$ to the intra-operative 3D C-arm CT image $I_2$.

Figure 9:
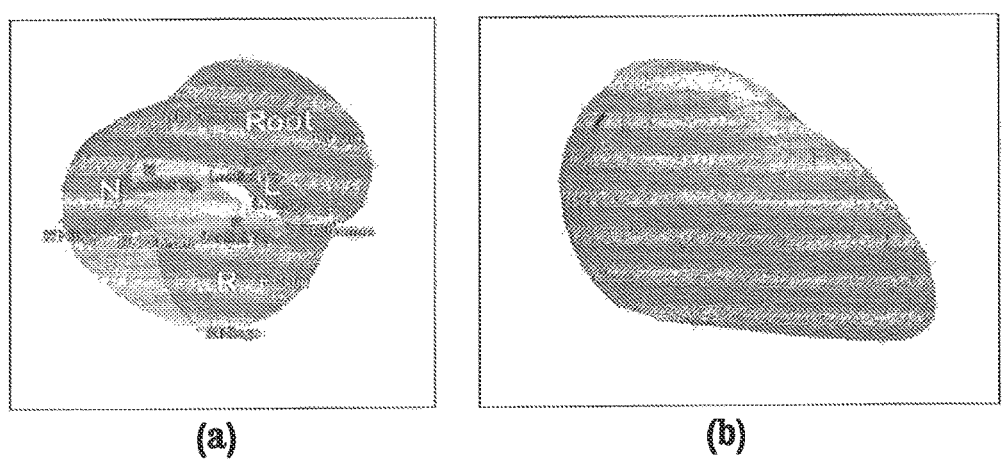
FIGS. 9(a)-(b) illustrates a model estimation derived from a pre-operative CT using discriminative machine learning techniques for the aortic valve and pericardium surface model, according to an embodiment of the invention.

Following the chronology of a typical clinical workflow, pre-operative structures $A_2$ and $T_2$ are treated as an input for the remainder of this disclosure. According to an embodiment of the invention, the pericardium is used as the anchor anatomy $A_1$ and $A_2$ and the aortic valve is used as the target anatomy $T_1$ and $T_2$. All models are estimated using robust, discriminative learning based methods, and final model estimations from pre-operative CT images $I_2$ are shown in FIG. 8. The precision of the final surface model for the pericardium is 1.91 mm±0.71 and for the aortic valve is 1.21 mm±0.21. FIGS. 9(a)-(b) illustrates a model estimation derived from a pre-operative CT $I_2$ using discriminative machine learning techniques for the aortic valve and pericardium surface model. FIG. 9(a) shows the aortic valve root, the leaflet tips, the hinges, the commissure points, and the ostias, while FIG. 9(b) shows the pericardium surface mesh model.

A method according to an embodiment of the invention can find an optimal transformation Φ that aligns the pre-operative structures $T_2$ and $A_2$ to the intra-operative image $I_1$:

$$\hat{\Phi} = \underset{\Phi}{\operatorname{argmax}} \, \log(P(\Phi \mid I_1, A_2)). \qquad (4)$$

The target structure $T_1$ is not visible in the intra-operative image, and therefore the transformation Φ is determined only through the anchor structures. Embodiments of the invention model Φ as a rigid transformation with six degrees of freedom.

The initial transformation $\Phi^0$ is approximated as a translation. A position detector can be trained using a probabilistic boosting tree classifier and Haar features on the barycenter $a_1$ of the anchor anatomy $A_1$ in the intra-operative image $I_1$. Thus $\Phi^0$ represents the translation between the barycenter $a_2$ of the anchor anatomy $A_2$ in the pre-operative image $I_2$ and the detected barycenter $a_1$ in the intra-operative image $I_1$.

Figure 11:
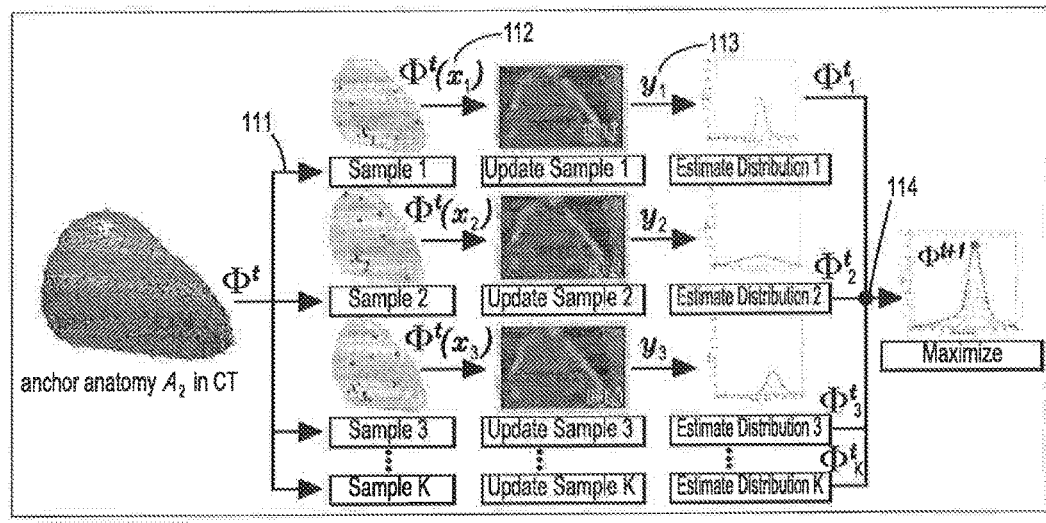
FIG. 11 illustrates one iteration of an EM approach according to an embodiment of the invention.

According to an embodiment of the invention, an expectation-maximization (EM) framework is used to determine the final parameters. FIG. 11 illustrates one iteration of an EM approach according to an embodiment of the invention to estimate the parameters of the transformation $\Phi^{t+1}$.

Referring now to FIG. 11, in an expectation stage, given a current estimate of the global transformation $\Phi^t$, K samples $\Phi_i^t$ point sets $(x_1, x_2, x_3, \ldots, x_K)$ are generated at step 111 from the pre-operative anchor anatomy $A_2$, where each point set comprises N points and each sample is represented as an isotropic 6D Gaussian distribution with $\mu_i$ representing the rigid transformation parameters and $\Sigma_i$ the uncertainty of the sample:

$$\Phi_i^t = N_6(\mu_i, \Sigma_i), \Sigma_i = \sigma_i I, \qquad (5)$$

where I is the identity matrix and $\sigma_i$ is a one dimensional variable calculated as a kernel function from the probability map F(I) evaluated at the point locations $y_{i,j}$, $i=1, \ldots, K$, $j=1, \ldots, N$.

Given the current estimate of the transformation $\Phi_i^t$ the point sets are transformed at step 112 into the intra-operative image $I_1$.

$$y^*_i = \Phi^t(x_i), i=1, \ldots, K. \qquad (6)$$

The mapped point sets are updated according to the image appearance of the intra-operative image $I_1$. Each point $y^*_{i,j}$, $j=1, \ldots, N$ from the point set $x_i$ is assigned a new location $y_{i,j}$, $j=1, \ldots, N$ based on the local image appearance.

Figure 10:
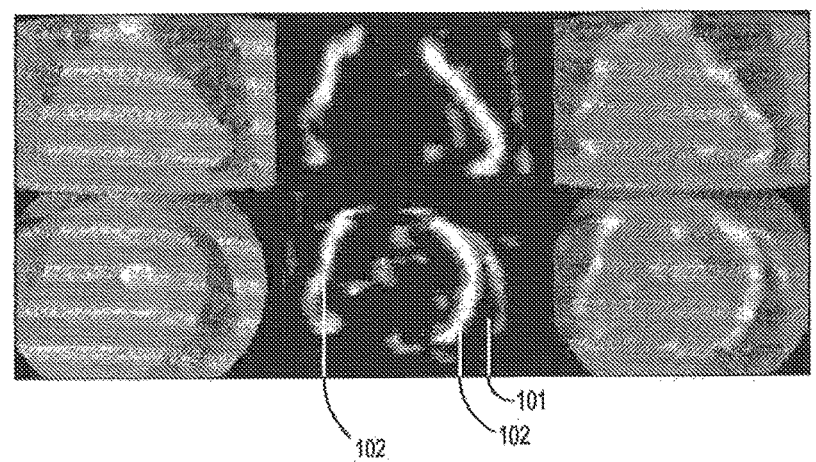
FIG. 10 shows the output of the boosting classifier response on the intra-operative 3D C-arm CT data trained to delineate certain boundary regions of the anchor anatomy, according to an embodiment of the invention.
Figure 23:
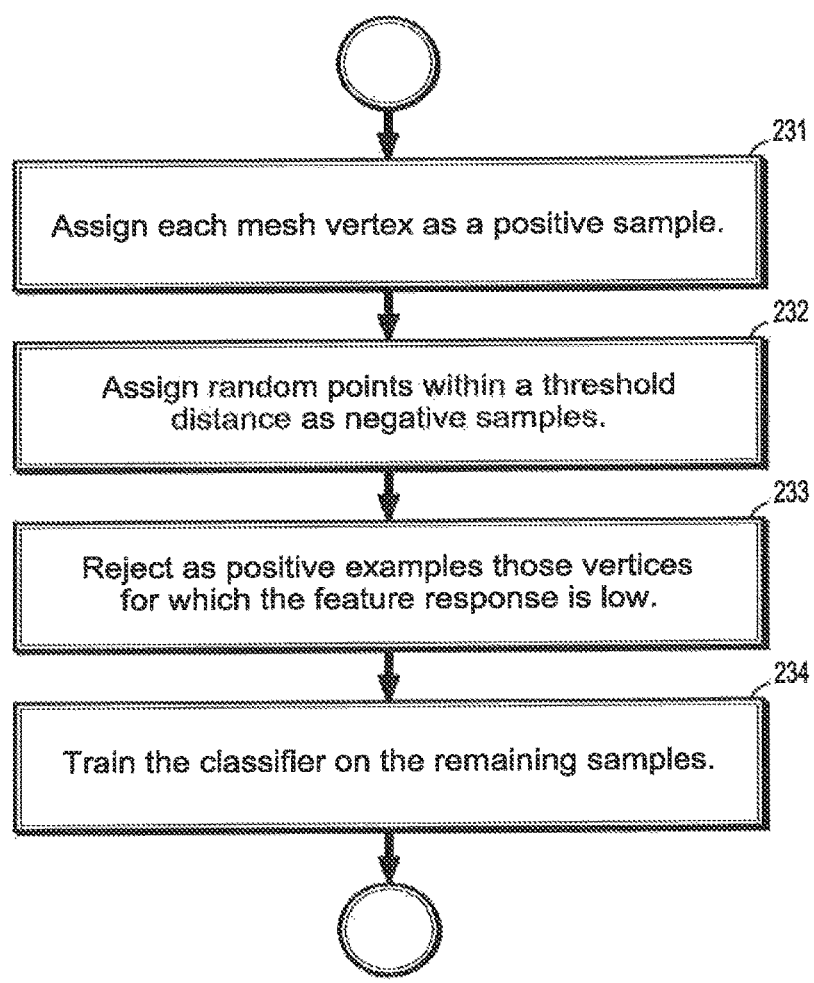
FIG. 23 is a flowchart of a method of deriving the probability map $F(I_1)$ from the intra-operative image $I_1$, according to an embodiment of the invention.

According to an embodiment of the invention, to secure a robust update schema a probability map $F(I_1)$ is used, which is derived from the intra-operative image $I_1$ by evaluating a boosting classifier trained using Haar features. The classifier can be trained using surface annotations of the anchor anatomy $A_1$ in the intra-operative image. A flowchart of a method according to an embodiment of the invention of deriving the probability map $F(I_1)$ from the intra-operative image $I_1$ is presented in FIG. 23. Referring now to the figure, each vertex can be assigned as a positive sample at step 231 and random points within a threshold distance can be used as negative samples at step 232. At step 233, those vertices for which the feature response of the Hessian is low are rejected as positive examples. The classifier is trained on the remaining samples at step 234. The output of the boosting classifier response on the intra-operative 3D C-arm CT data $F(I_1)$ trained to delineate certain boundary regions of the anchor anatomy A1 (pericardium) is shown in FIG. 10. Uncertain regions 101 such as the boundary between the pericardium and the liver have low response while the transition 102 from the pericardium and the lung have high confidence.

Referring again to FIG. 11, the final parameters of each sample $\Phi_i^t$ are approximated at step 113 by an isotropic Gaussian distribution. The mean μ is computed from a least squares solution between the point set in the pre-operative data $(x_1, x_2, x_3, \ldots, x_K)$ and the updated point set $(y_1, y_2, y_3, \ldots, y_K)$ in the intra-operative image $I_1$ by minimizing the mapping error function $e_i$ $$e_i = \frac{1}{N} \sum_{j=1}^{N} \|\Phi_i^t(x_{i,j}) - y_{i,j}\|. \qquad (7)$$

In a maximization stage, the values of the global transformation $\Phi^t$ are updated at step 114 based on the estimated mixture model $$\oplus = \sum_{i=1}^{K} \Phi_i^t$$

of the K transformation samples $\Phi_i^t$, $i=1, \ldots, K$:

$$\Phi^{t+1} = \underset{\Phi}{\operatorname{argmax}}(\Phi \mid \Phi^t) \qquad (8)$$

As there is no analytic solution, embodiments employ a mean shift algorithm to approximate the solution.

Figure 24:
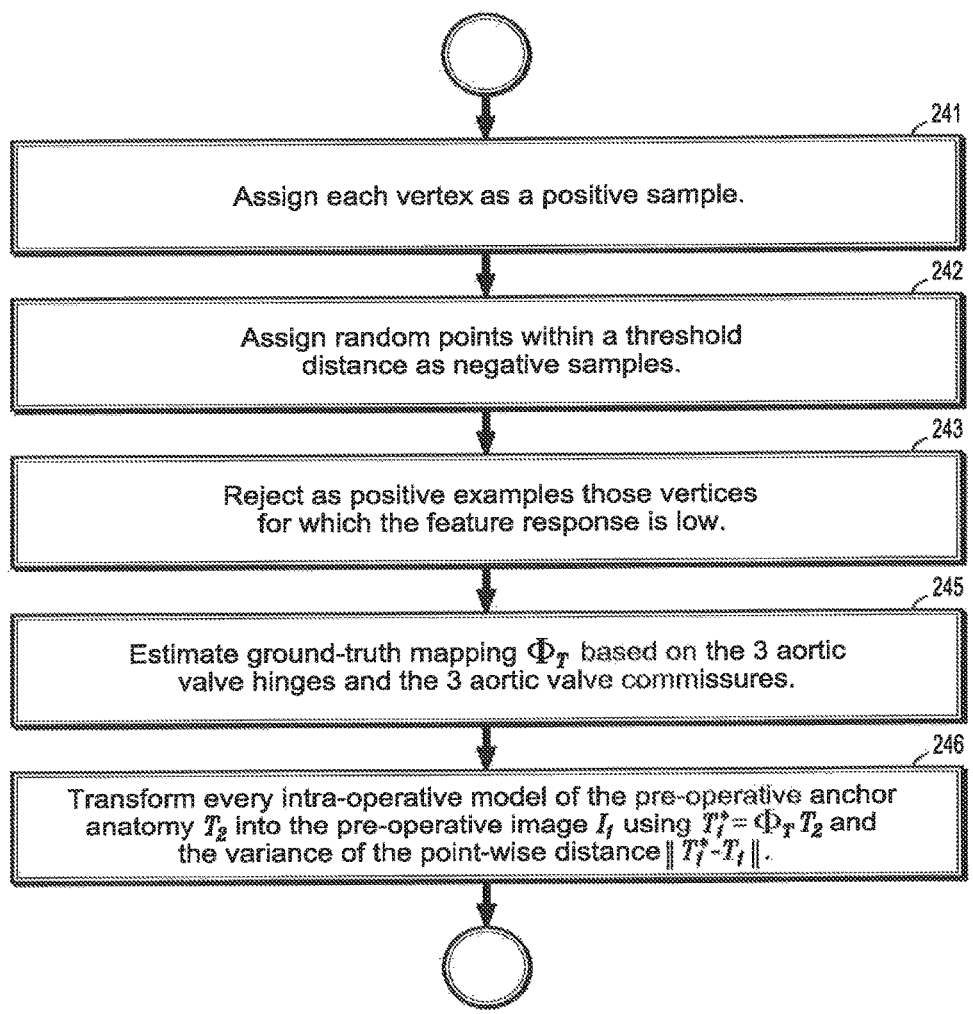
FIG. 24 is a flowchart of a method of estimating a prior probability for each mesh point of the pre-operative image models, according to an embodiment of the invention.

To minimize a mapping error with regard to the target anatomy $T_1$ and $T_2$, embodiments estimate a prior probability for each mesh point of the pre-operative image models. According to an embodiment of the invention, this information can be incorporated into the expectation phase where random points can be sampled on the pre-operative anchor model $A_2$. A flowchart of a method according to an embodiment of the invention of estimating a prior probability for each mesh point of the pre-operative image models is presented in FIG. 24. Referring now to the figure, each vertex can be assigned as a positive sample at step 241 and random points within a threshold distance can be used as negative samples at step 242. At step 243, those vertices for which the feature response of the Hessian is low are rejected as positive examples. Based on the 3 aortic valve hinges and the 3 aortic valve commissures, depicted in FIG. 9(a), a ground-truth mapping $\Phi_T$ is estimated at step 245. At step 246, every intra-operative model of the pre-operative anchor anatomy $T_2$ is transformed to the pre-operative image $I_1$ using $T^*_1 = \Phi_T T_2$ and the variance of the point-wise distance $\|T^*_1 - T_1\|$.

FIG. 12 illustrates prior weights indicating the significance of each vertex for an accurate mapping with respect to the target anatomy T, the aortic valve. Reference number 121 indicates high probability regions while reference number 122 indicates low probability locations. Most of the significant area is located around the left atrium, while the left ventricle shows low confidence for the location of the aortic valve. FIG. 12 confirms that certain regions on the anchor anatomy may better approximate the desired transformation Φ between the target anatomies than others. Points on the left atrium may align the pre-operative and intra-operative images with respect to the target anatomy $T_1$ and $T_2$, the aortic valve.

EXPERIMENTS

A method according to an embodiment of the invention for probe pose detection was validated on synthetic, phantom and in vivo datasets. Throughout the experiments a GE Linear TTE Transducer was used. The synthetic dataset includes 4050 simulated fluoroscopy images generated by means of DRR from a 3D C-arm rotational angiography volume of the TEE probe, which cover the entire search space of out-plane parameters. The volume size was 512×512×4330 with 0.2225 mm per slice. The ground-truth was generated by annotating the 3D probe position in the rotational angiography volume and projecting it into the simulated fluoroscopy images. The phantom dataset includes a rotational angiography volume of the TEE probe inserted into a silicon phantom, and a total of 51 fluoroscopic images captured by rotating the C-arm and keeping the TEE probe static. The position of the C-arm is known from the robotic control, which enabled the ground-truth to be computed for each fluoroscopic image from a 3D probe annotation, similar to the synthetic data. The in vivo dataset was acquired during several porcine studies and includes 50 fluoroscopic sequences comprising of about 7,000 frames, which cover an extensive range of probe angulations. The pose parameters were manually annotated in all sequences and corresponding frames, and assumed as ground-truth for training and testing.

In a first experiment, the quantitative and qualitative performance evaluation of the in-plane parameter (u, v, θy) detection was performed on all three datasets. The detector was trained on 75% of the in vivo dataset (36 sequences of 5,363 frames) and tested on the entire synthetic, phantom and remaining 25% of the in vivo dataset. The results are summarized in Table 1, shown in FIG. 13. In the table, the numbers in parentheses are standard deviations.

For the in vivo data the average in-plane position (u, v) error was 2.2 and 3.7 mm, respectively, and the in-plane orientation error was 6.69 degrees. Errors in the position estimation are caused by false detections along the shaft of the probe. False position detections contribute to errors in the orientation estimation. The true positive rate is 0.88 and the false positive rate is 0.22. The detection and accuracy is affected by dose level, proximity to dense tissue and background clutter. For a detection framework according to an embodiment of the invention, the probe should be clearly distinguishable from its background. FIGS. 14(a)-(d) illustrate detection examples and nature of in vivo images with cluttered background and low textured probe, as indicated by the box and arrow 140 in each image.

The results for the phantom and synthetic data are provided in Table 1 where detection was performed at a fixed scale. The Fluoro data from the phantom experiment appears different from the in vivo data used to train the detectors making it challenging. The true positive rate was 0.95 and false positive rate 0.05. False detections were caused by the density of the silicon phantom, which obscures the probe in three images. The true positive and false positive rates for synthetic data were 0.99 and 0.01 respectively. The visual appearance of the synthetic DRR is different from the training data, however the probe is distinguishable causing high true positive rate.

The out-of-plane (θr, θp) detectors are analyzed on the synthetic data to evaluate the accuracy of the binary template matching. FIG. 15 plots the (θr, θp) error in mm over the search space in degrees and illustrates stable detection with a single outlier.

Finally a framework according to an embodiment of the invention was evaluated with respect to all parameters. Quantitative validation was performed on synthetic and phantom data, as ground truth data for in vivo data was not available. The results are summarized in Table 2, shown in FIG. 16. In the table, the numbers in parentheses are standard deviations. The largest error is in the Z axis, which corresponds to the optical axis of the Fluoro device. It is expected that this would be the largest error because estimating distance along the optical axis is challenging from a monocular Fluoro image. Fortunately, the goal of the framework is to visualize anatomy in the Fluoro image, therefore errors in Z has little effect on the final visualization. Qualitative evaluation is performed on in vivo Fluoro images, depicted in FIG. 17, which are Fluoro images showing the detected pose of the probe, indicated by the arrows 170.

The computational performance was evaluated for an Intel 2.13 GHz single core with 3.4 GB of RAM. The average detection time is 0.53 seconds. The computational cost can be reduced by incorporating temporal information to reduce the search space.

To illustrate the clinical relevance of a method according to an embodiment of the invention, an anatomical model of the mitral valve is detected in a 3D TEE and visualized in Fluoro. FIG. 18(a) is a Fluoro image of the catheter, FIG. 18(b) depicts the mitral detected in 3D TEE, and FIG. 18(c) shows the valve model visualized in Fluoro. The modalities are not synchronized and are manually fused. The catheter 180 can be seen in both modalities.

A further experiment was performed to validate a mapping Φ according to an embodiment of the invention from pre-operative CT to an intra-operative 3D C-arm CT used 37 patient pairs (74 volumes). According to an embodiment of the invention, contrasted intra-operative 3D C-arm CT were used as the aortic valve can be manually annotated and used for quantitative comparisons. All ground-truth annotations were obtained by expert users manually placing anatomical landmarks and the full surface models of the target and anchor anatomies in the pre- and intra-operative images. The estimation errors can be assessed from Table III, shown in FIG. 19, which displays the system precision for the estimation of target anatomy $T_1=\Phi(T_2)$. The error is evaluated as the deviation of the transformed target anatomy $\Phi(T_2)$ and the ground-truth annotation $T_{1,GT}$. A sparse matching method according to an embodiment of the invention using a prior sampling scheme has the best performance. It is more accurate than standard rigid registration algorithms using a mutual information metric, and the transformation Φ extracted from the annotated anchor anatomies $A_1$ and $A_2$. The reason may be that a C-arm CT contains many uncertain regions of the anchor anatomy without clear contrast at the anatomy border. Thus, user annotations are not consistent between the two modalities and produce a larger mapping error than our fully automated method.

FIG. 20 shows several examples of fused volumes with a mapped aortic valve model 201 detected in pre-operative CT $I_2$ and mapped into the non-contrasted intra-operative 3D C-arm CT $I_1$ using a sparse matching method with prior sampling according to an embodiment of the invention. For clarity, the model outline 201 is indicated in only one of the images of FIG. 20. The first row shows different volume cuts with the estimated target $T_2$ and anchor $A_2$ anatomies. The middle and bottom rows show the aligned anchor $A_1$ and target $T_1$ anatomies. Left image shows an example of 1.86 mm and right 4.03 mm error of the mapped target anatomy when compared to the ground truth annotation.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 21:
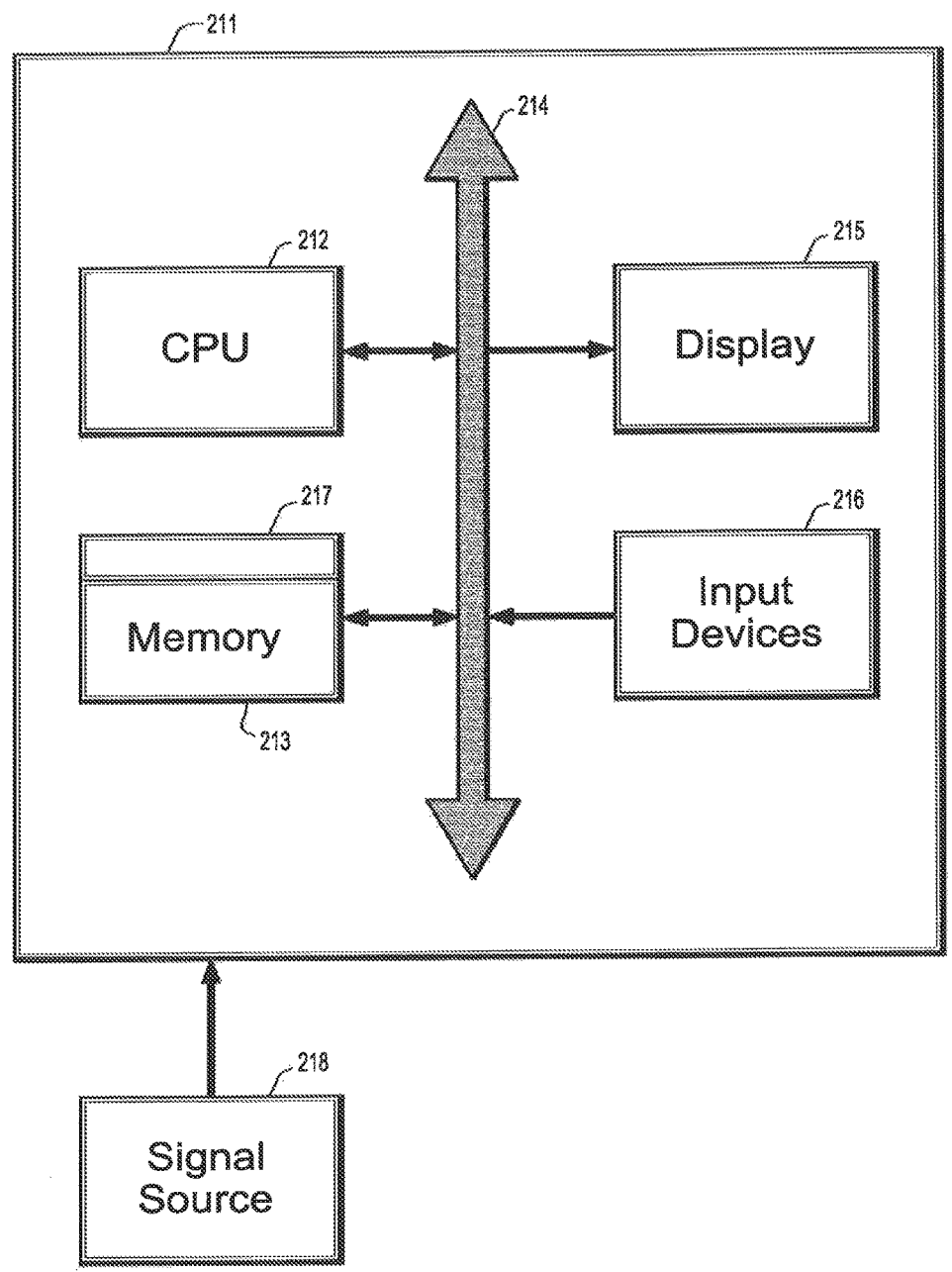
FIG. 21 is a block diagram of an exemplary computer system for fusing images for interventional guidance, according to an embodiment of the invention.

FIG. 21 is a block diagram of an exemplary computer system for implementing a system for fusing images for interventional guidance, according to an embodiment of the invention. Referring now to FIG. 21, a computer system 211 for implementing the present invention can comprise, inter alia, a central processing unit (CPU) 212, a memory 213 and an input/output (I/O) interface 214. The computer system 211 is generally coupled through the I/O interface 214 to a display 215 and various input devices 216 such as a mouse and a keyboard. The support circuits can include circuits such as cache, power supplies, clock circuits, and a communication bus. The memory 213 can include random access memory (RAM), read only memory (ROM), disk drive, tape drive, etc., or a combinations thereof. The present invention can be implemented as a routine 217 that is stored in memory 213 and executed by the CPU 212 to process the signal from the signal source 218. As such, the computer system 211 is a general purpose computer system that becomes a specific purpose computer system when executing the routine 217 of the present invention.

The computer system 211 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method of transforming target structure anatomies in a pre-operative image $I_2$ into an intra-operative image $I_1$, comprising the steps of:

determining a transformation $\Phi$ aligns a target structure $T_2$ and an anchor structure $A_2$ in the pre-operative image $I_2$ into a corresponding target structure $T_1$ and anchor structure $A_1$ in the intra-operative image $I_1$ by finding a transformation $\hat{\Phi}$ that maximizes a functional $\log(P(\Phi|I_1, A_2))$ using an expectation-maximization approach, wherein the target structure $T_1$ is not visible in the intra-operative image, using the transformation $\hat{\Phi}$ to fuse the pre-operative image $I_2$ with the intra-operative image $I_1$ to create fused image wherein the target structure $T_2$ is visible in the fused image.

2. The method of claim 1, wherein said transformation $\Phi$ is a rigid transformation, wherein an initial transformation $\Phi^0$ is approximated as a translation, wherein $\Phi^0$ represents a translation between a barycenter $a_2$ of the anchor anatomy $A_2$ in the pre-operative image $I_2$ and a detected barycenter $a_1$ of the anchor anatomy $A_1$ in the intra-operative image $I_1$.

3. The method of claim 2, wherein initial transformation $\Phi^0$ is determined by a position detector trained by a probabilistic boosting tree classifier and Haar features on the barycenter $a_1$ of the anchor anatomy $A_1$ in the intra-operative image $I_1$.

4. The method of claim 1, wherein a pericardium is used as the anchor anatomy $A_1$ and $A_2$ and the aortic valve is used as the target anatomy $T_1$ and $T_2$.

5. The method of claim 1, wherein finding a transformation $\hat{\Phi}$ that maximizes a functional $\log(P(\Phi|I_1, A_2))$ comprises:

generating K sample $\Phi_i^t$ point sets $(x_1, x_2, x_3, \ldots, x_K)$ from the pre-operative anchor anatomy $A_2$, wherein each point set comprises N points and each sample is represented as an isotropic 6D Gaussian distribution $\Phi_i^t = N_6(\mu_i, \Sigma_i)$, $\Sigma_i = \sigma_i I$, wherein I is an identity matrix and $\sigma_i$ is a one dimensional variable calculated as a kernel function from a probability map $F(I)$ evaluated at the point locations $y_{i,j}$, $i=1, \ldots, K$, $j=1, \ldots, N$;

transforming the point sets $\Phi_i^t$ into the intra-operative image $I_1$ locations $y^*_{i} = \Phi^t(x_i)$, $i=1, \ldots, K$, according to an appearance of the intra-operative image $I_1$, assigning each point $y^*_{i,j}$, $j=1, \ldots, N$ from the point set $x_i$ to a new location $y_{i,j}$, $j=1, \ldots, N$, based on a local appearance of the intra-operative image $I_1$, approximating final parameters of each sample $\Phi_i^t$ by an isotropic Gaussian distribution, wherein a mean $\mu$ is computed from a least squares solution between the point set $\Phi_i^t$ in the pre-operative $I_2$ and the updated point set $(y_1, y_2, y_3, \ldots, y_K)$ in the intra-operative image $I_1$ by minimizing a mapping error function $$e_i = \frac{1}{N} \sum_{j=1}^{N} \|\Phi_i^t(x_{i,j}) - y_{i,j}\|;$$

and determining an updated global transformation $\Phi^{t+1}$ from $$\Phi^{t+1} = \underset{\Phi}{\operatorname{argmax}}(\Phi \mid \Phi^t)$$

based on an estimated mixture model $$\oplus = \sum_{i=1}^{K} \Phi_i^t$$

of the K transformation samples $\Phi_i^t$, i=1, . . . , K.

6. The method of claim 5, wherein $$\Phi^{t+1} = \underset{\Phi}{\mathrm{argmax}}(\Phi \mid \Phi^t)$$

is estimated using a mean shift algorithm.

7. The method of claim 5, further comprising deriving the probability map $F(I_1)$ from the intra-operative image $I_1$ by evaluating a boosting classifier trained using Haar features and surface annotations of the anchor anatomy $A_1$ in the intra-operative image $I_1$, wherein each vertex of a model of the intra-operative image $I_1$ is assigned as a positive sample and random points within a threshold distance are used as negative samples, and those vertices for which a feature response is low are rejected as positive examples.

8. The method of claim 7, wherein minimizing said mapping error further comprises estimating a prior probability for each vertex of a model of pre-operative image $I_2$ by assigning each vertex of a model of the pre-operative image $I_2$ as a positive sample and using random points within a threshold distance as negative samples, rejecting those vertices for which a feature response is low as positive examples, estimating a ground-truth mapping $\Phi_T$ based on hinges and commissures of the aortic valve, and transforming each intra-operative model of the pre-operative anchor anatomy $T_2$ into the pre-operative image $I_1$ using $T^*_1 = \Phi_T T_2$ and the variance of a point-wise distance $\|T^*_1 - T_1\|$.

9. A non-transitory program storage device readable by a computer, tangibly embodying a program of instructions executed by the computer to perform the method steps for transforming target structure anatomies in a pre-operative image $I_2$ into an intra-operative image $I_1$, the method comprising the steps of:
   determining a transformation $\Phi$ aligns a target structure $T_2$ and an anchor structure $A_2$ in the pre-operative image I2 into a corresponding target structure $T_1$ and anchor structure $A_1$ in the intra-operative image $I_1$ by finding a transformation $\hat{\Phi}$ that maximizes a functional $\log(P(\Phi|I_1,A_2))$ using an expectation-maximization approach, wherein the target structure $T_1$ is not visible in the intra-operative image,
   using the transformation $\hat{\Phi}$ to fuse the pre-operative $I_2$ with the intra-operative image $I_1$ to create a fused image wherein the target structure $T_2$ is visible in the fused image.

10. The computer readable program storage device of claim 9, wherein said transformation $\Phi$ is a rigid transformation, wherein an initial transformation $\Phi^0$ is approximated as a translation, wherein $\Phi^0$ represents a translation between a barycenter $a_2$ of the anchor anatomy $A_2$ in the pre-operative image $I_2$ and a detected barycenter $a_1$ of the anchor anatomy $A_1$ in the intra-operative image $I_1$.

11. The computer readable program storage device of claim 10, wherein initial transformation $\Phi^0$ is determined by a position detector trained by a probabilistic boosting tree classifier and Haar features on the barycenter $a_1$ of the anchor anatomy $A_1$ in the intra-operative image $I_1$.

12. The computer readable program storage device of claim 9, wherein a pericardium is used as the anchor anatomy $A_1$ and $A_2$ and the aortic valve is used as the target anatomy $T_1$ and $T_2$.

13. The computer readable program storage device of claim 9, wherein finding a transformation $\hat{\Phi}$ that maximizes a functional $\log(P(\Phi|I_1,A_2))$ comprises:
   generating K sample $\Phi_i^t$ point sets $(x_1, x_2, x_3, \ldots, x_K)$ from the pre-operative anchor anatomy $A_2$, wherein each point set comprises N points and each sample is represented as an isotropic 6D Gaussian distribution $\Phi_i^t = N_6(\mu_i, \Sigma_i)$, $\Sigma_i = \sigma_i I$, wherein I is an identity matrix and $\sigma_i$ is a one dimensional variable calculated as a kernel function from a probability map $F(I)$ evaluated at the point locations $y_{i,j}$, i=1, . . . , K, j=1, . . . , N;
   transforming the point sets $\Phi_i^t$ into the intra-operative image $I_1$ locations $y^*_i = \Phi^t(x_i)$, i=1, . . . , K, according to an appearance of the intra-operative image $I_1$;
   assigning each point $y^*_{i,j}$, j=1, . . . , N from the point set $x_i$ to a new location $y_{i,j}$, j=1, . . . , N, based on a local appearance of the intra-operative image $I_1$;
   approximating final parameters of each sample $\Phi_i^t$ by an isotropic Gaussian distribution, wherein a mean $\mu$ is computed from a least squares solution between the point set $\Phi_i^t$ in the pre-operative $I_2$ and the updated point set $(y_1, y_2, y_3, \ldots, y_K)$ in the intra-operative image h by minimizing a mapping error function $$e_i = \frac{1}{N} \sum_{j=1}^{N} \|\Phi_i^t(x_{i,j}) - y_{i,j}\|;$$

and
determining an updated global transformation $\Phi^{t+1}$ from $$\Phi^{t+1} = \underset{\Phi}{\mathrm{argmax}}(\Phi \mid \Phi^t)$$

based on an estimated mixture model $$\oplus = \sum_{i=1}^{K} \Phi_i^t$$

of the K transformation samples $\Phi_i^t$, i=1, . . . , K.

14. The computer readable program storage device of claim 13, wherein $$\Phi^{t+1} = \underset{\Phi}{\mathrm{argmax}}(\Phi \mid \Phi^t)$$

is estimated using a mean shift algorithm.

15. The computer readable program storage device of claim 13, the method further comprising deriving the probability map $F(I_1)$ from the intra-operative image $I_1$ by evaluating a boosting classifier trained using Haar features and surface annotations of the anchor anatomy $A_1$ in the intra-operative image $I_1$, wherein each vertex of a model of the intra-operative image $I_1$ is assigned as a positive sample and random points within a threshold distance are used as negative samples, and those vertices for which a feature response is low are rejected as positive examples.

16. The computer readable program storage device of claim 15, wherein minimizing said mapping error further comprises estimating a prior probability for each vertex of a model of pre-operative image $I_2$ by assigning each vertex of a model of the pre-operative image $I_2$ as a positive sample and using random points within a threshold distance as negative samples, rejecting those vertices for which a feature response is low as positive examples, estimating a ground-truth mapping $\Phi_T$ based on hinges and commissures of the aortic valve, and transforming each intra-operative model of the pre-operative anchor anatomy $T_2$ into the pre-operative image $I_1$ using $T^*_1 = \Phi_T T_2$ and the variance of a point-wise distance $\|T^*_1 - T_1\|$.

* * * * *